(12) United States Patent
Von Unge et al.

(10) Patent No.: US 8,697,880 B2
(45) Date of Patent: Apr. 15, 2014

(54) COMPOUNDS USEFUL FOR THE SYNTHESIS OF S- AND R-OMEPRAZOLE AND A PROCESS FOR THEIR PREPARATION

(75) Inventors: Sverker Von Unge, Fjärås (SE); Christina Fregler, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 493 days.

(21) Appl. No.: 12/329,077

(22) Filed: Dec. 5, 2008

(65) Prior Publication Data

US 2009/0253911 A1 Oct. 8, 2009

Related U.S. Application Data

(60) Division of application No. 11/689,801, filed on Mar. 22, 2007, now abandoned, which is a continuation of application No. 11/060,138, filed on Feb. 17, 2005, now abandoned.

(30) Foreign Application Priority Data

Feb. 20, 2004 (SE) .................................. 0400410-7

(51) Int. Cl.
C07D 401/12 (2006.01)

(52) U.S. Cl.
USPC ...................................................... 546/273.7

(58) Field of Classification Search
USPC ...................................................... 546/273.7
See application file for complete search history.

(56) References Cited

U.S. PATENT DOCUMENTS

| | | | |
|---|---|---|---|
| 5,929,244 A | 7/1999 | von Unge | |
| 5,948,789 A | 9/1999 | Larsson et al. | |
| 6,002,011 A | 12/1999 | Kato et al. | |
| 6,303,787 B1 | 10/2001 | Prasad | |
| 6,982,275 B2 | 1/2006 | Hashimoto et al. | |
| 7,169,799 B2 | 1/2007 | Hashimoto et al. | |
| 2005/0187256 A1 | 8/2005 | von Unge et al. | |
| 2007/0161682 A1 | 7/2007 | von Unge et al. | |
| 2008/0255199 A1 | 10/2008 | Fregler et al. | |

FOREIGN PATENT DOCUMENTS

| | | |
|---|---|---|
| EP | 5129 B1 | 4/1981 |
| EP | 124495 B1 | 11/1984 |
| EP | 484265 A1 | 5/1992 |
| EP | 652872 B1 | 5/1995 |
| ES | 2187248 | 8/2000 |
| JP | 2001-507025 | 5/2001 |
| JP | H10-504290 | 6/2001 |
| PT | 102361 A | 3/2001 |
| WO | WO-92/08716 | 5/1992 |
| WO | WO-94/27988 | 12/1994 |
| WO | WO-96/02535 | 2/1996 |
| WO | WO-98/28294 | 7/1998 |
| WO | WO 98/40377 | 9/1998 |
| WO | WO-98/40378 | 9/1998 |
| WO | WO-01/04109 | 1/2001 |
| WO | WO-03/089408 A2 | 10/2003 |
| WO | WO-03/097606 A1 | 11/2003 |
| WO | WO-2005/054228 A1 | 6/2005 |
| WO | WO-2005/080374 | 9/2005 |

OTHER PUBLICATIONS

Hanna Cotton et al., "Asymmetric synthesis of esomeprazole", Tetrahedron: Asymmetry 11 (2000) 3819-3825.
Per Erlandsson; "Resolution of the enantiomers of omeprazole and some of its analogues . . . "; Journal of Chromatography, 532 (190) pp. 305-319.
Muljibhai et al., "Process for Preparation, etc.," Chemical Abstracts, ISSN:0009-2258; No. 11; vol. 147 :235177 (2003).

Primary Examiner — Patricia L Morris
(74) Attorney, Agent, or Firm — David M. Gryte

(57) ABSTRACT

The present invention relates to an improved method for the synthesis of the (S)- or (R)-enantiomer of omeprazole, characterized in that 2-[[(4-X-3,5-dimethylpyridin-2-yl)methyl]thio]-5-methoxy-1H-benzimidazole or 2-[[(4-X-3,5-dimethyl-1-oxidopyridin-2-yl)methyl]thio]-5-methoxy-1H-benzimidazole, wherein X is a leaving group, is oxidized into the corresponding sulphoxide which is obtained as a crystalline compound. Recrystallization of the thus obtained sulphoxide results in a compound of enhanced chemical and optical purity, which is subsequently transformed into the (S)- or (R)-enantiomer of omeprazole.

7 Claims, No Drawings

COMPOUNDS USEFUL FOR THE SYNTHESIS OF S- AND R-OMEPRAZOLE AND A PROCESS FOR THEIR PREPARATION

This application is a divisional of U.S. patent application Ser. No. 11/689,801, filed 22 Mar. 2007 now abandoned, which is a continuation of U.S. patent application Ser. No. 11/060,138, filed 17 Feb. 2005, abandoned.

FIELD OF THE INVENTION

The present invention is directed to new compounds of high optical purity, a process for their preparation and their use as intermediates in the synthesis of the S- or R-enantiomer of 5-methoxy-2-[[(4-methoxy-3,5-dimethyl-2-pyridinyl)methyl]sulphinyl]-1H-benzimidazole.

BACKGROUND OF THE INVENTION

The compound 5-methoxy-2-[[(4-methoxy-3,5-dimethyl-2-pyridinyl)methyl]sulphinyl]-1H-benzimidazole, having the generic name omeprazole, and therapeutically acceptable alkaline salts thereof are described in EP 5129 and EP 124 495, respectively. Omeprazole and its alkaline salts are effective gastric acid secretion inhibitors, and are useful as antiulcer agents. The compounds, being sulphoxides, have an asymmetric center in the sulphur atom, i.e. exist as two optical isomers (enantiomers). It has been shown that the magnesium salt of the S-enantiomer of omeprazole has better pharmacokinetic and metabolic properties compared to omeprazole, and this is described in EP 0 652 872 B 1. As a result of this the magnesium salt of the S-enantiomer of omeprazole has an improved therapeutic profile such as a lower degree of interindividual variation.

In EP 0 773 940 B1 a process for preparation of the single enantiomers of omeprazole and structurally related sulphoxides is described. In this process, a pro-chiral sulphide is oxidised with an oxidising agent in the presence of a chiral titanium complex into the corresponding sulphoxide either as a single enantiomer or in enantiomerically enriched form.

Single enantiomers of omeprazole in neutral form are difficult to obtain in crystalline state and thus these compounds are most frequently obtained as non crystalline products. In for instance WO 92/08716 the neutral form of the R enantiomer of omeprazole is obtained as an amorphous solid and in WO 94/27988 both of the enantiomers of omeprazole—in their neutral forms—are obtained in the form of syrups or oils. In WO 94/27988 is also described the preparation of alkaline salts of the single enantiomers, which are obtainable as crystalline products. These can be purified by recrystallisation resulting in products of very high optical purity. Furthermore, optically pure salts of the S-enantiomer of omeprazole are stable towards racemization both in neutral pH and basic pH.

WO 98/28294 discloses S-omeprazole in neutral form that is in a solid state.

It would be desirable to perform the oxidation of pro-chiral sulphides yielding highly crystalline sulphoxide intermediates, thus making it possible to directly recrystallise the crude sulphoxides in its neutral form in order to increase the optical purity as well as to increase the chemical purity. The purified enantiomerically enriched sulphoxide intermediates could then be converted into the S- or R-enantiomer of omeprazole and thereafter optionally into pharmaceutically acceptable salts thereof. An advantage of such a process is that a requisite chemical and optical purification step would not involve the addition of an alkaline medium to a titanium containing reaction mixture, which process is associated with problems with the formation of inorganic titanium salts that are difficult to work with. A further advantage is if the titanium catalyzed reaction step occurs earlier in the synthesis of the enantiomerically enriched compounds thereby reducing a possible risk of contamination of the final product by titanium salts.

The present invention relates to new crystalline sulphoxides which are stable enough to be directly recrystallised, the preparation of these sulphoxides and their use as intermediates in the synthesis of S- and R-enantiomer of omeprazole.

DETAILED DESCRIPTION OF THE INVENTION

The present invention refers to new highly crystalline sulphoxides in enantiomerically enriched form which are chemically stable enough to be directly crystallised from an oxidation reaction mixture, the preparation of these sulphoxides and their use as intermediates in the synthesis of the S- and R-enantiomer of omeprazole and pharmaceutically acceptable salts thereof.

According to another aspect of the invention, the new synthetic intermediates are defined by formula I either as a single enantiomer or in enantiomerically enriched form:

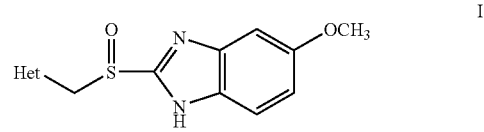

wherein
Het is

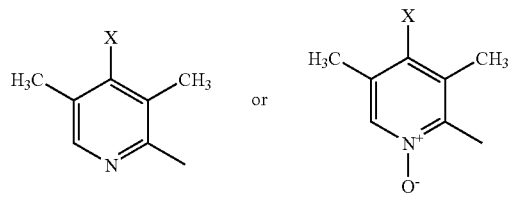

and X is a leaving group such as a halogen (F, Cl, Br, I), $NO_2$, $N_2^+$ or $-OSO_2R$ (R is $CH_3$, $CF_3$, p-toluene, m-chlorobenzene, p-chlorobenzene).

According to another aspect of the invention the leaving group X is chloro or nitro as in the compounds of formula Ia, Ib, Ic and Id:

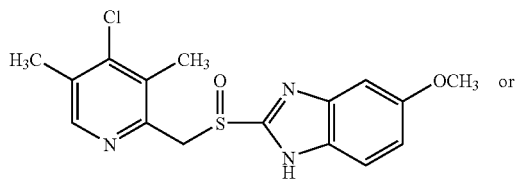

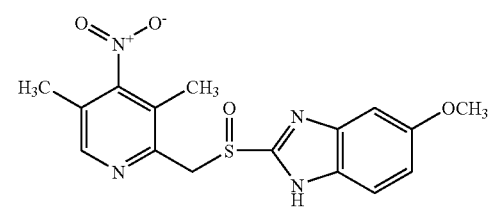

-continued

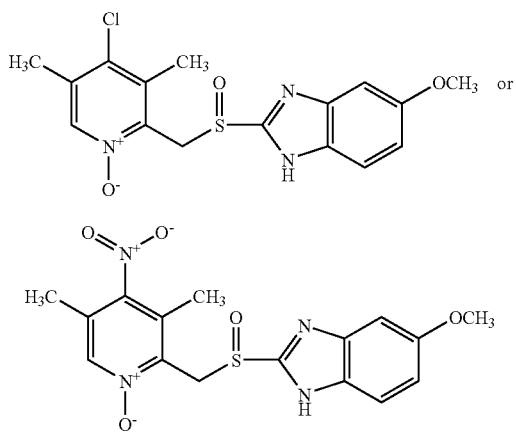

The compounds Ia-Id, and their corresponding tautomers, exist either as a single enantiomer or in an enantiomerically enriched form.

A further aspect of the invention is the preparation of compounds of formula I, which can be used as intermediates in the synthesis of the S- and R-enantiomer of omeprazole and pharmaceutically acceptable salts thereof. The preparation of the compounds of formula I may be carried out as described in EP 0 773 940 B 1, and this is also illustrated in Scheme 1 below.

Scheme 1

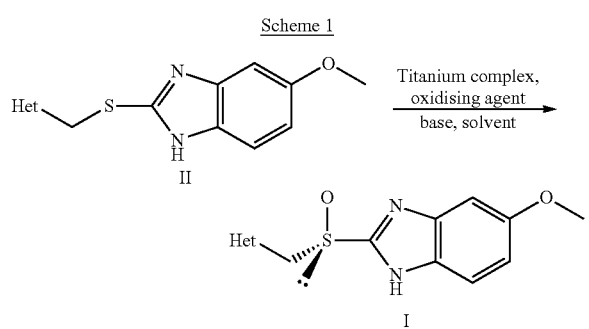

wherein Het is

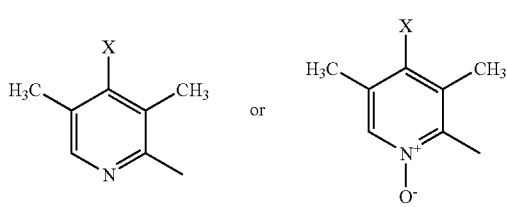

and X is a leaving group such as a halogen (F, Cl, Br, I), $NO_2$, $N_2^+$ or $-OSO_2R$ (R is $CH_3$, $CF_3$, p-toluene, m-chlorobenzene, p-chlorobenzene).

In this process, a pro-chiral sulphide such as II is oxidised in an organic solvent with an oxidising agent, e.g. cumene hydroperoxide, in the presence of a chiral titanium complex. The titanium complex suitable for catalysing the process of the invention is prepared from a chiral ligand and a titanium(I) compound such as preferably a titanium(IV) alkoxide, and optionally in the presence of water. The chiral ligand used in the preparation of the titanium complex is for instance a chiral alcohol such as a chiral diol. The oxidation may be performed in the presence of a base, e.g. N,N-diisopropylethylamine.

The oxidation is carried out in an organic solvent. The solvent can be chosen with respect to suitable conditions from an industrial point of view as well as environmental aspects. Suitable organic solvents are for instance toluene, ethyl acetate, methyl ethyl ketone, methyl isobutyl ketone, diethyl carbonate, tert.butyl methyl ether, tetrahydrofurane, methylene chloride and the like. From an environmental point of view non-chlorinated solvents are preferred.

The oxidation is preferably carried out in an organic solvent at room temperature or just above room temperature, e.g. between 20-40° C. If the reaction time is varied a reaction temperature may be chosen below as well as above the preferred temperatures 20-40° C. A suitable temperature range is limited only depending on the decomposition of the compounds, and that the reaction time is dramatically shorter at room temperature than at −20° C. since the sulphides of interest are oxidised very slowly at such a low temperature.

An oxidising agent suitable for this asymmetric oxidation may be a hydroperoxide, such as for example tert.-butylhydroperoxide or cumene hydroperoxide, preferably the latter. The titanium complex suitable for catalysing the process of the invention is prepared from a chiral ligand and a titanium(IV) compound such as preferably titanium(IV) alkoxide, and optionally in the presence of water. An especially preferred titanium(IV) alkoxide is titanium(IV) isopropoxide or -propoxide. The amount of the chiral titanium complex is not critical. An amount of less than approximately 0.50 equivalents is preferred and especially preferred amount is 0.05-0.30 equivalents. Even very low amounts of complex, such as for instance 0.04 equivalents may be used in the processes according to the present invention with excellent result.

The titanium complex may also be prepared by reacting titanium tetrachloride with a chiral ligand in the presence of a base.

The chiral ligand used in the preparation of the titanium complex is preferably a chiral alcohol such as a chiral diol. The diol may be a branched or unbranched alkyl diol, or an aromatic diol. Preferred chiral diols are esters or tartaric acid, especially (+)-diethyl L-tartrate or (−)-diethyl D-tartrate are preferred.

The chiral titanium complex may be prepared in the presence of the pro-chiral sulphide or before the pro-chiral sulphide is added to the reaction vessel.

According to one aspect of the invention, the oxidation is carried out in the presence of a base. The base may be an inorganic or an organic base, such as for instance a hydrogen carbonate, an amide or an amine. Amine includes a guanidine or an amidine. Organic bases are preferred and especially suitable bases are amines, preferably triethylamine or N,N-diisopropylethylamine. The amount of base added to the reaction mixture is not critical but should be adjusted with respect to the reaction mixture.

The preparation of the chiral titanium complex is preferably performed in the presence of the pro-chiral sulphide.

Other essential features in the preparation of the chiral titanium complex is that the preparation of the complex is performed during an elevated temperature and/or a prolonged time. With an elevated temperature is meant a temperature above room temperature, such as for instance 30-70° C., preferably 40-60° C. A prolonged preparation time is a period of time longer than approximately 20 minutes, preferably 1-5 hours. A suitable period of time for the preparation step depends on the preparation temperature and of the pro-chiral sulphide, optionally present during the preparation of the chiral titanium complex.

Yet a further aspect of the invention is the conversion of compounds of formula I into the S- and R-enantiomer of omeprazole and pharmaceutically acceptable salts thereof. Scheme 2 and Scheme 3 below describe synthetic routes for converting compound I into the S-enantiomer of omeprazole. The same routes can be applied to convert compound I into the R-enantiomer of omeprazole provided that the chirality of the chiral titanium complex used in the oxidising reaction step is changed to the opposite of that used for making the corresponding S-enantiomer.

Scheme 2

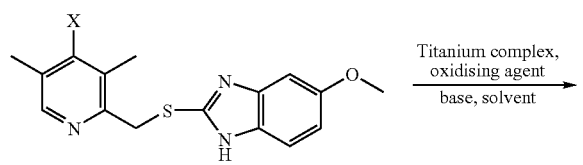

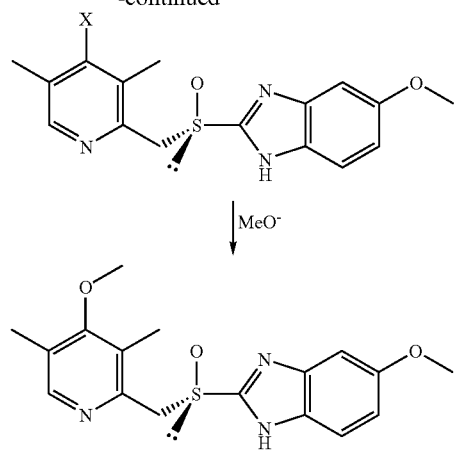

In Scheme 2, the first step is performed as described above. The obtained sulphoxide I may be recrystallised in order to enhance chemical and optical purity. Finally, a substitution reaction with methoxide, e.g. sodium methoxide, yields the S-enantiomer of omeprazole, which may be converted to a pharmaceutically acceptable salt thereof Scheme 3

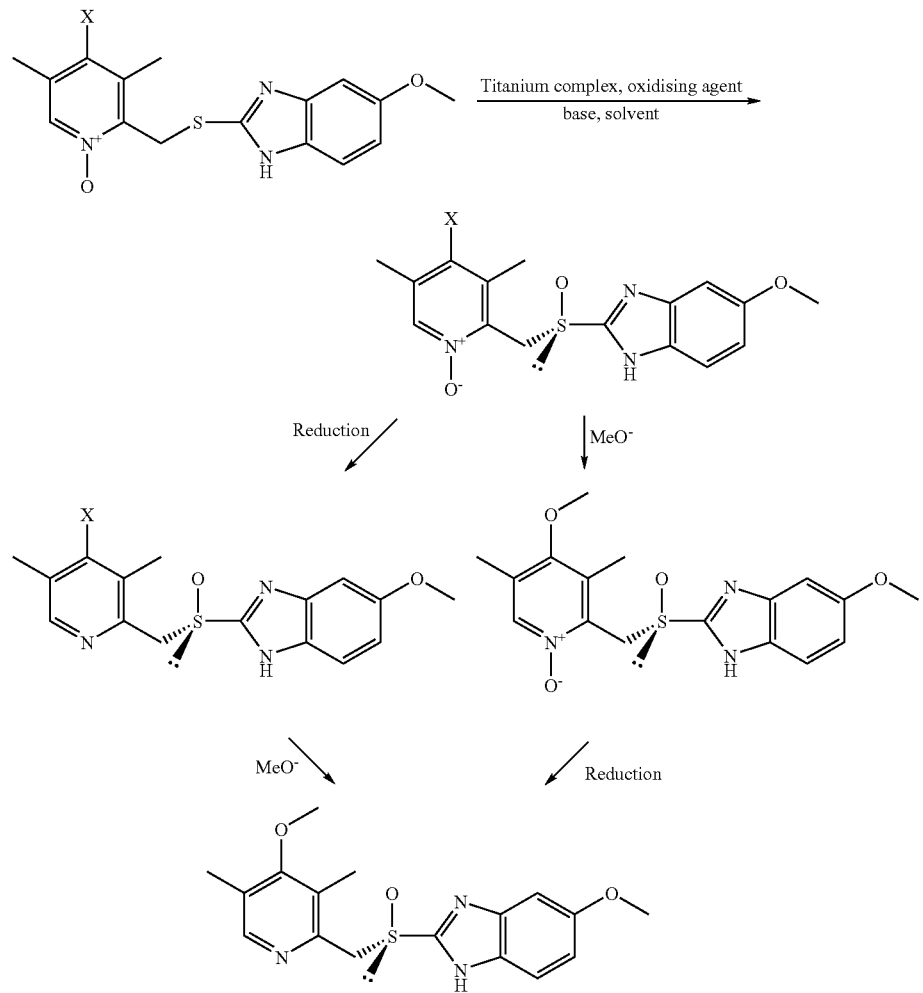

In Scheme 3, the first step is performed as described above. Nucleophilic substitution of the leaving group X with methoxide, e.g. sodium methoxide, is thereafter performed prior to or after reduction of the pyridine-N-oxide to pyridine.

The compounds of the invention may exist as tautomers. It is to be understood that the present invention encompasses all such tautomers.

The invention is illustrated by the following non-limiting examples.

EXAMPLE 1

Synthesis of (S)-2-[[(4-chloro-3,5-dimethyl-2-pyridinyl)methyl]sulfinyl]5-methoxy-1H-benzimidazole 1.2 g (3.6 mmol) of 2-{[(4-chloro-3,5-dimethyl-2-pyridinyl)methyl]thio}-5-methoxy-1H-benzimidazole was mixed with toluene (40 mL). The mixture was concentrated until half the volume was left. Water (38 mg, 2.1 mmol), (S,S)-diethyl tartrate (1.85 g, 9.0 mmol) and titanium tetraisopropoxide (1.0 g, 3.6 mmol) were added in the given order while stirring. The mixture was then stirred at 50° C. for an hour and then N,N-diisopropylethylamine (0.46 g, 3.6 mmol) was added at room temperature. After 15 minutes cumene hydroperoxide (80% in cumene, 0.69 g, 3.6 mmol) was added dropwise and stirring was then continued for 2 h at room temperature. The optical purity of crude sulfoxide turned out to be 75% ee as determined by chiral HPLC analysis of the solution. The mixture was washed with water and then evaporated. The product was purified by chromatography on silica gel using methanol/dichloromethane as eluent (gradient, 1-7% MeOH) and this afforded 1.0 g of a crude product as a solid. Recrystallisation from hot acetonitrile gave 0.35 g of a white solid with an enantiomeric excess of 51%. Next, the mother liqueur from the filtration was concentrated and this material was then also recrystallised from acetonitrile to give 0.35 g of the title compound as a crystalline product with an enantiomeric excess of 92.5%.

$^1$H NMR of the most enriched fraction (92.5% ee) in chloroform-d; 2.3 (s, 3H), 2.4 (s, 3H), 3.8 (s, 3H), 4.8 (AB-system, 2H), 7.0 (dd, 1H), 7.0 (b, 1H), 7.5 (b, 1H), 8.2 (s, 1H).

EXAMPLE 2

Synthesis of (S)-2-[[(4-nitro-3,5-dimethyl-2-pyridinyl)methyl]sulfinyl]5-methoxy-1H-benzimidazole In an analogous experiment as in Example 1—starting from 1.2 g of (S)-2-[[(4-nitro-3,5-dimethyl-2-pyridinyl)methyl]thio]5-methoxy-1H-benzimidazole—1.0 g of the title compound as a crystalline product was obtained. The enantiomeric excess of this crude product was determined to be 48% by chiral HPLC analysis.

The invention claimed is:

1. A compound of formula I in the form of a single enantiomer, a tautomer of the single enantiomer, an enantiomerically enriched form of the compound, or a tautomer of the enantiomerically enriched form of the compound,

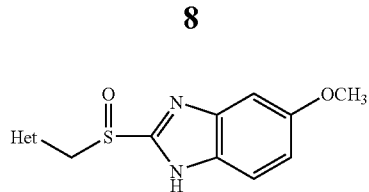

wherein the compound is in a crystalline form, and wherein Het is

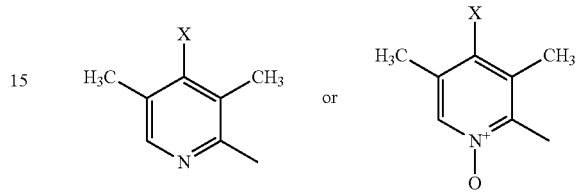

and X is a leaving group selected from the group consisting of a halogen, $NO_2$, $N_2^+$ and $OSO_2R$, wherein R is selected form the group consisting of $CH_3$, $CF_3$, p-toluene, m-chlorobenzene, and p-chlorobenzene.

2. The compound 2-[[(4-chloro-3,5-dimethyl-2-pyridinyl)methyl]sulfinyl]5-methoxy-1H-benzimidazole in the form of a single enantiomer, a tautomer of the single enantiomer, an enantiomerically enriched form of the compound, or a tautomer of the enantiomerically enriched form of the compound, wherein the compound is in a crystalline form.

3. The compound 2-[[(4-nitro-3,5-dimethyl-2-pyridinyl)methyl]sulfinyl]5-methoxy-1H-benzimidazole in the form of a single enantiomer, a tautomer of the single enantiomer, an enantiomerically enriched form of the compound, or a tautomer of the enantiomerically enriched form of the compound, wherein the compound is in a crystalline form.

4. The compound 2-[[(4-chloro-3,5-dimethyl-1-oxidopyridin-2-yl)methyl]sulfinyl]-5-methoxy-1H-benzimidazole in the form of a single enantiomer, a tautomer of the single enantiomer, an enantiomerically enriched form of the compound, or a tautomer of the enantiomerically enriched form of the compound wherein the compound is in a crystalline form.

5. The compound 2-[[(4-nitro-3,5-dimethyl-1-oxidopyridin-2-yl)methyl]sulfinyl]-5-methoxy-1H-benzimidazole in the form of a single enantiomer, a tautomer of the single enantiomer, an enantiomerically enriched form of the compound, or a tautomer of the enantiomerically enriched form of the compound, wherein the compound is in a crystalline form.

6. The compound (S)-2-[[(4-chloro-3,5-dimethyl-2-pyridinyl)methyl]sulfinyl]5-methoxy-1H-benzimidazole, wherein the compound is in a crystalline form.

7. The compound (S)-2-[[(4-nitro-3,5-dimethyl-2-pyridinyl)methyl]sulfinyl]5-methoxy-1H-benzimidazole, wherein the compound is in a crystalline form.

* * * * *